(12) United States Patent  
Gourabi et al.

(10) Patent No.: US 10,962,518 B2  
(45) Date of Patent: Mar. 30, 2021

(54) DISSOLUTION TEST FOR SENSITIVE DRUGS

(71) Applicants: Hamid Gourabi, Tehran (IR); Hamid Mobedi, Tehran (IR); Siyavash Mirzaei, Tehran (IR); Sakineh Khezli, Qods (IR)

(72) Inventors: Hamid Gourabi, Tehran (IR); Hamid Mobedi, Tehran (IR); Siyavash Mirzaei, Tehran (IR); Sakineh Khezli, Qods (IR)

(73) Assignees: ROYAN INSTITUTE, Tehran (IR); IRAN POLYMER AND PETROCHEMICAL INSTITUTE, Tehran (IR)

( * ) Notice: Subject to any disclaimer, the term of this patent is extended or adjusted under 35 U.S.C. 154(b) by 318 days.

(21) Appl. No.: 16/172,794

(22) Filed: Oct. 28, 2018

(65) Prior Publication Data

US 2019/0101518 A1 Apr. 4, 2019

Related U.S. Application Data

(60) Provisional application No. 62/578,397, filed on Oct. 28, 2017.

(51) Int. Cl.  
*B01L 7/00* (2006.01)  
*B01L 7/02* (2006.01)  
(Continued)

(52) U.S. Cl.  
CPC ................ *G01N 33/15* (2013.01); *B01L 7/02* (2013.01); *B01L 7/525* (2013.01); (Continued)

(58) Field of Classification Search  
CPC ............ G02B 2005/1804; G02B 5/021; G02B 5/0278; G02B 5/0284; G02B 5/22; (Continued)

(56) References Cited

U.S. PATENT DOCUMENTS

2006/0288805 A1* 12/2006 Das .................. G01N 33/15  
                                                            73/866  
2007/0092404 A1*  4/2007 Hughes ............... G01N 13/00  
                                                            422/68.1

FOREIGN PATENT DOCUMENTS

EP          1308724 A2 *  5/2003  ............. G01N 33/15

* cited by examiner

*Primary Examiner* — Jennifer Wecker  
(74) *Attorney, Agent, or Firm* — Bajwa IP Law Firm; Haris Zaheer Bajwa

(57) ABSTRACT

A method and apparatus for drug dissolution testing may include an overflow vessel with an overflow outlet port at a predetermined height from a bottom of the overflow vessel, a first water bath submerging the overflow vessel and configured to keep a temperature of the overflow vessel at a first predetermined temperature, a pressurized vessel containing a dissolution medium, a second water bath submerging the pressurized vessel and configured to keep the dissolution medium at a second predetermined temperature, a dissolution medium path with an output end connected in fluid communication with the flow cell and an input end attached in fluid communication to the pressurized vessel, where the dissolution medium path may transfer the dissolution medium from the pressurized vessel into the flow cell, a collection vessel connected to the overflow outlet port of the flow cell, and a third water bath submerging the collection vessel and configured to keep the collection vessel at a third predetermined temperature.

18 Claims, 8 Drawing Sheets

(51) Int. Cl.
  *G03F 7/20* (2006.01)
  *G01N 33/15* (2006.01)
(52) U.S. Cl.
  CPC .............. *B01L 2200/0621* (2013.01); *B01L 2300/0681* (2013.01); *B01L 2300/087* (2013.01); *B01L 2400/0457* (2013.01); *B01L 2400/0487* (2013.01)
(58) Field of Classification Search
  CPC ..... G03F 1/24; G03F 1/42; G03F 1/44; G03F 7/706; G03F 7/70683; G03F 9/7076; B01L 2200/0621; B01L 2300/0681; B01L 2300/087; B01L 2400/0457; B01L 2400/0487; B01L 7/02; B01L 7/525; G01N 33/15
  See application file for complete search history.

DISSOLUTION TEST FOR SENSITIVE DRUGS

CROSS-REFERENCE TO RELATED APPLICATION

This application claims the benefit of priority from U.S. Provisional Patent Application Ser. No. 62/578,397, filed on Oct. 28, 2017, and entitled "DISSOLUTION TEST APPARATUS FOR SENSITIVE DRUGS (DTASD)," which is incorporated herein by reference in its entirety.

TECHNICAL FIELD

The present disclosure relates to systems and methods for dissolution testing in the pharmaceutical industry, and particularly to systems and methods for evaluating the dissolution performance of drugs that are sensitive to environmental conditions.

BACKGROUND

Dissolution testing is among several important testing procedures that a pharmaceutical product should undergo to gain qualitative and quantitative approval. Dissolution testing may be utilized as either a quality control tool to monitor and ensure batch-to-batch conformity of oral dosage forms or a drug development tool to predict in-vivo performance of a pharmaceutical product. Dissolution tests are utilized as substitutes for human studies. Analytical data obtained from drug dissolution tests may be used to test or monitor the efficacy of a pharmaceutical product without the need for performing in-vivo tests.

The dissolution testing involves putting a dosage form in contact with a dissolution medium to allow a targeted chemical contained in the dosage form to dissolve in the dissolution medium and form a sample solution. Sample solutions that are collected from the dissolution tests may then be analyzed by analysis methods such as ultraviolet-visible spectrophotometry (UV-Vis) or high performance liquid chromatography (HPLC).

Evaluating the dissolution performance of drugs that are sensitive to environmental conditions is one of the challenges in controlled drug delivery systems. Many sensitive drugs such as proteins and peptides can be degraded in the dissolution media in a short time. Thus, in sustained-release drug delivery systems (SRDDS), evaluating the dissolution and rate of release under human physiological conditions (37° C.) and for long periods (up to several months) may be time-consuming and expensive due to the instability and sensitivity of these drugs to physiological conditions. This means that when the existing pharmacopoeia dissolution test apparatuses are used to perform the dissolution tests for SRDDSs that contain temperature-sensitive drugs, the frequency of the sampling needs to be high and the test time needs to be short. Besides, the samples should immediately be prepared for analysis after sampling. For example, if in a SRDDS, the stability of a pharmaceutical molecule in the dissolution medium at a temperature of approximately 37° C. is 2 hours, the test time for the pharmaceutical molecule should be less than 2 hours. In this case, since the dissolution test for this group of products is usually evaluated for 24 hours, sampling, sample preparation, and sample analysis should be performed more than 12 times within 24 hours. Thus, if a 3-month release time is needed for such a system, then, the number of sampling, sample preparation, and analyses for a drug product will be more than 1080 times. Performing this number of tests for just one pharmaceutical product requires a great deal of time, energy, and cost.

There is, therefore, a need for reducing the number of required tests to a reasonable amount by stabilizing temperature-sensitive drugs under the above-mentioned conditions. Consequently, there is a need for development of dissolution test systems and methods that may allow for maximizing the stability of the sensitive drugs.

SUMMARY

This summary is intended to provide an overview of the subject matter of the present disclosure, and is not intended to identify essential elements or key elements of the subject matter, nor is it intended to be used to determine the scope of the claimed implementations. The proper scope of the present disclosure may be ascertained from the claims set forth below in view of the detailed description below and the drawings.

According to one or more exemplary embodiments, the present disclosure is directed to an exemplary apparatus for drug dissolution testing that may include an overflow vessel with an overflow outlet port at a predetermined height from a bottom of the overflow vessel, a first water bath submerging the overflow vessel and configured to keep a temperature of the overflow vessel at a first predetermined temperature, a pressurized vessel containing a dissolution medium, a second water bath submerging the pressurized vessel and configured to keep the dissolution medium at a second predetermined temperature, a dissolution medium path with an output end connected in fluid communication with the flow cell and an input end attached in fluid communication to the pressurized vessel, where the dissolution medium path may transfer the dissolution medium from the pressurized vessel into the flow cell, a collection vessel connected to the overflow outlet port of the flow cell, and a third water bath submerging the collection vessel and configured to keep the collection vessel at a third predetermined temperature.

In an exemplary embodiment, the output end of the dissolution medium path may be positioned within the overflow vessel adjacent the bottom of the overflow vessel. The dissolution medium may be injected into the overflow vessel via the dissolution medium path. In an exemplary embodiment, the dissolution medium may be injected into the overflow vessel via the dissolution medium path with a flow rate between 0.1 mL/h and 1000 mL/h.

In an exemplary embodiment, the pressurized vessel may include a dissolution medium reservoir containing a dissolution medium, and a dissolution medium pump in fluid communication with the dissolution reservoir. The dissolution medium pump may be configured to pressurize the dissolution medium.

In an exemplary embodiment, the flow cell may include a dosage form placed at the bottom of the overflow vessel below the overflow outlet port and a released drug sample may be obtained by putting the dosage form in contact with the dissolution medium within the flow cell.

In an exemplary embodiment, the overflow outlet port may allow a continuous discharge of the released drug sample responsive to a height of released drug sample reaching the predetermined height.

In an exemplary embodiment, the overflow vessel may further include a filter positioned at the overflow outlet port. The filter may be configured to retain undissolved dosage form within the vertical overflow vessel.

In an exemplary embodiment, the first predetermined temperature may be equal to the second predetermined temperature. In an exemplary embodiment, the second predetermined temperature may be 37±1° C. In an exemplary embodiment, the third predetermined temperature may be between 2 and 8° C.

According to one or more exemplary embodiments, the present disclosure is directed to an exemplary method for drug dissolution testing that may include heating a dissolution medium to a second predetermined temperature, obtaining a released drug sample by putting the heated dissolution medium in contact with a dosage form. Putting the heated dissolution medium in contact with the dosage form may include continuously injecting the heated dissolution medium into an overflow vessel with an overflow outlet port at a predetermined height from a bottom of the vertical overflow vessel and the dosage form may be placed at the bottom of the vertical overflow vessel below the overflow outlet port, and collecting the obtained released drug sample in a collection vessel at a third predetermined temperature. The overflow vessel may be kept at the second predetermined temperature by submerging the overflow vessel in a water bath at the second predetermined temperature.

In an exemplary embodiment, exemplary method for drug dissolution testing may further include retaining undissolved dosage form within the vertical overflow vessel by filtering the obtained released drug sample.

In an exemplary embodiment, the second predetermined temperature may be 37±1° C. In an exemplary embodiment, the third predetermined temperature may be between 2 and 8° C.

BRIEF DESCRIPTION OF THE DRAWINGS

The drawing figures depict one or more implementations in accord with the present teachings, by way of example only, not by way of limitation. In the figures, like reference numerals refer to the same or similar elements.

DETAILED DESCRIPTION

Figure 1:
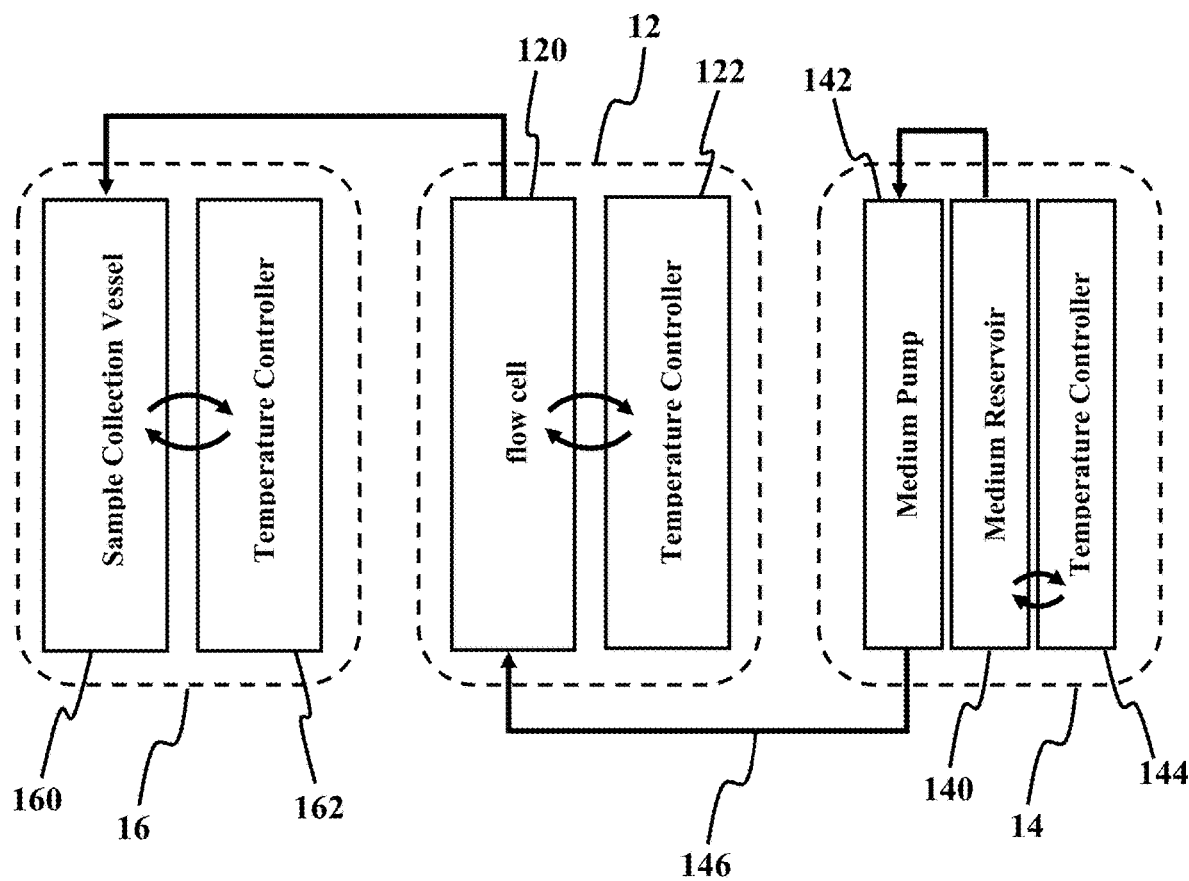
FIG. 1 illustrates a dissolution test system, consistent with one or more exemplary embodiments of the present disclosure.

In the following detailed description, numerous specific details are set forth by way of examples to provide a thorough understanding of the relevant teachings related to the exemplary embodiments. However, it should be apparent that the present teachings may be practiced without such details. In other instances, well known methods, procedures, components, and/or circuitry have been described at a relatively high-level, without detail, in order to avoid unnecessarily obscuring aspects of the present teachings.

The following detailed description is presented to enable a person skilled in the art to make and use the methods and devices disclosed in exemplary embodiments of the present disclosure. For purposes of explanation, specific nomenclature is set forth to provide a thorough understanding of the present disclosure. However, it will be apparent to one skilled in the art that these specific details are not required to practice the disclosed exemplary embodiments. Descriptions of specific exemplary embodiments are provided only as representative examples. Various modifications to the exemplary implementations will be plain to one skilled in the art, and the general principles defined herein may be applied to other implementations and applications without departing from the scope of the present disclosure. The present disclosure is not intended to be limited to the implementations shown, but is to be accorded the widest possible scope consistent with the principles and features disclosed herein.

The present disclosure is directed to exemplary systems and methods for performing dissolution tests for drugs, food and other chemical compounds that are sensitive to temperature. Exemplary systems and methods may allow for applying an optimal temperature control throughout the dissolution testing procedure on both the dissolution process and the sample solution obtained from the dissolution process.

Exemplary dissolution test systems for temperature-sensitive drugs may include a release environment where a dosage form such as a pill, tablet, capsule, syrup, etc., may be put in contact with a release medium or a dissolution medium. The dissolution medium may be continuously pumped into the release environment by a dissolution pump from a dissolution reservoir. Fresh dissolution medium may continuously be put in contact with the dosage form and a sample solution may continuously be collected in a sample reservoir or a collecting vessel. The sample solution may contain a targeted active chemical contained in the dosage form which is dissolved into the dissolution medium. Exemplary dissolution testing systems for temperature-sensitive drugs may further include temperature control mechanisms for the dissolution medium, the release environment, and the collected sample solution. In exemplary embodiments, by controlling the temperature of the dissolution medium and the release environment at a predetermined similar value, a temperature shock may be avoided when the dissolution medium is added to the dosage form in the release environment. A temperature shock may be harmful to sensitive drug molecules in the release environment. Therefore, in exemplary dissolution testing systems, the temperature of the dissolution medium may be increased to the temperature of the release environment before the dissolution medium is injected into the release environment. The exemplary dissolution testing systems may allow for the dissolution medium to be added to the drug dosage disposed within the release medium with a controlled temperature and flow rate.

In an exemplary embodiment, the targeted active chemical contained in the dosage form in the release environment may gradually be released into the dissolution medium and form the sample solution which may be gradually collected in the sample reservoir or the collecting vessel. In an exemplary embodiment, by controlling the temperature of the collected sample solution in the sample reservoir or the collecting vessel, a longer stability of the collected sample may be ensured. In order to stabilize the collected sample for longer periods, the temperature of the collected sample solution may be kept at a temperature condition under which the targeted chemical shows a longer stability than under the release environment condition. Furthermore, for further improving the stability of the targeted chemical, stabilizers such as 2,4,5-Trihydroxymethamphetamine (THMA) may also be added to the collected sample solution.

The exemplary dissolution testing systems may allow for obtaining more reliable dissolution test results for the temperature-sensitive drugs and since these sensitive drugs may be stabilized for longer periods, fewer tests may be required for monitoring the sustained release of these drugs in relatively longer periods.

FIG. 1 illustrates a dissolution test system 10, consistent with one or more exemplary embodiments of the present disclosure. In an exemplary embodiment, FIG. 1 illustrates a block diagram of dissolution test system 10 to illustrate the functionality of the overall system and may not be reflective of the exemplary structure of dissolutions system 10. Dissolution test system 10 may include a release environment assembly 12 that may be utilized for putting a dosage form in contact with a dissolution medium, a dissolution medium supply assembly 14 that may be utilized for supplying a continuous flow of fresh dissolution medium into release environment assembly 12, and a sample collection assembly 16 that may be utilized for continuously collecting a released-drug sample solution obtained from release environment assembly 12.

In an exemplary embodiment, release environment assembly 12 may include a flow cell 120 that may provide a release environment in which the dissolution medium may be put in contact with the dosage form to allow the dosage form to be gradually released into the dissolution medium and form a sample solution. In an exemplary embodiment, release environment assembly 12 may further include a first temperature controller 122 that may be utilized for controlling and maintaining a temperature of flow cell 120 at a first predetermined temperature. A first predetermined temperature may be 37±1° C. similar to human body temperature.

In an exemplary embodiment, dissolution medium supply assembly 14 may include a dissolution medium reservoir 140 that may contain a fresh dissolution medium. Dissolution medium supply assembly 14 may further include a dissolution medium pump 142 that may be connected in fluid communication with dissolution medium reservoir 140 and flow cell 120. In an exemplary embodiment, dissolution medium pump 142 may be utilized for pressurizing and injecting the fresh dissolution medium from dissolution medium reservoir 140 into flow cell 120.

In an exemplary embodiment, dissolution medium supply assembly 14 may further include a second temperature controller 144 that may be utilized for controlling and maintaining a temperature of dissolution medium reservoir 140 at a second predetermined temperature. The second predetermined temperature may be similar to the first predetermined temperature in order to avoid a temperature shock when the dissolution medium is injected to the flow cell 120 to contact the dosage form in the release environment. As mentioned before, a temperature shock may be harmful to sensitive drug molecules in the release environment, therefore, in an exemplary embodiment, the temperature of dissolution medium reservoir 140 may be controlled and maintained at 37±1° C. by second temperature controller 144.

In an exemplary embodiment, dissolution medium reservoir 140 together with dissolution medium pump 142 may form a pressurized dissolution medium reservoir that may be in fluid communication with flow cell 120 via a dissolution medium path 146.

In an exemplary embodiment, sample collection assembly 16 may include a sample collection vessel 160 that may be connected in fluid communication with a discharge of flow cell 120 and may collect the sample solution that contains a targeted chemical released from the dosage form into the dissolution medium. In an exemplary embodiment, sample collection assembly 16 may further include a third temperature controller 162 that may be utilized for controlling and maintaining a temperature of sample collection vessel 160 at a third predetermined temperature. The third predetermined temperature may be a temperature at which the targeted chemical contained in the dosage form is the most stable based on stability tests that may be performed on the dosage form at different temperatures. In an exemplary embodiment, the third predetermined temperature may be in a range of 2° C. to 8° C.

Figure 2A:
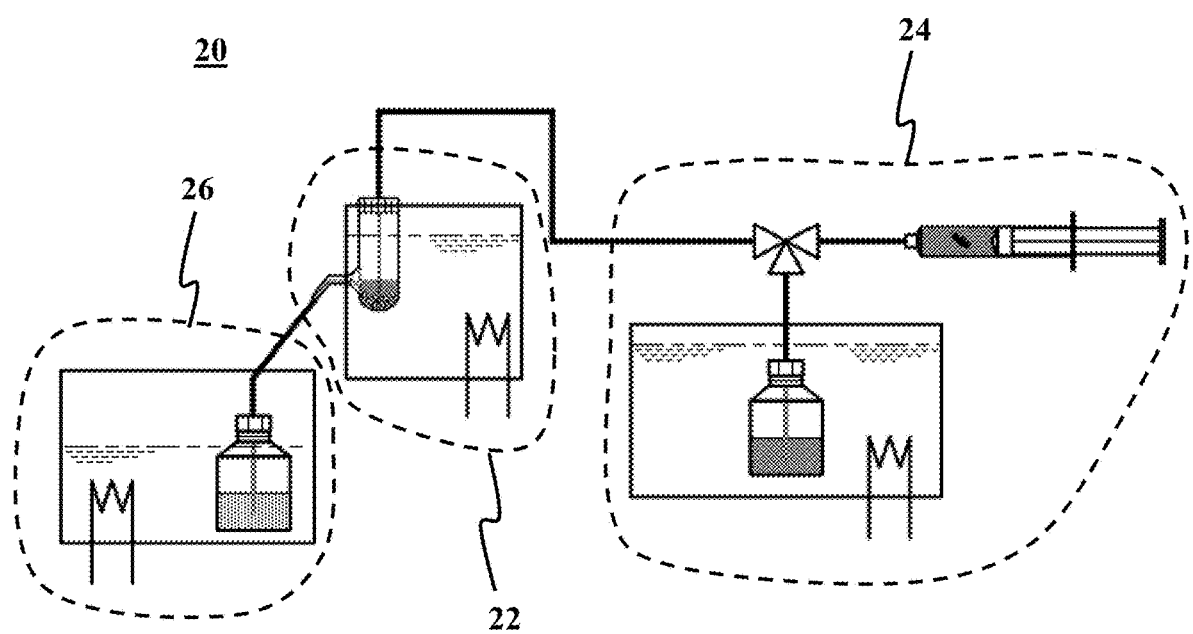
FIG. 2A illustrates a dissolution test apparatus, consistent with one or more exemplary embodiments of the present disclosure.

FIG. 2A illustrates a dissolution test apparatus 20, consistent with one or more exemplary embodiments of the present disclosure. Dissolution test apparatus 20 may be similar to dissolution test system 10 of FIG. 1. Referring to FIGS. 1 and 2A, in an exemplary embodiment, dissolution test apparatus 20 may include a release environment assembly 22 similar to release environment assembly 12 that may be utilized for putting a dosage form in contact with a dissolution medium, a dissolution medium supply assembly 24 similar to dissolution medium supply assembly 14 that may be utilized for supplying a continuous flow of fresh dissolution medium into release environment assembly 22, and a sample collection assembly 26 similar to sample collection assembly 16 that may be utilized for continuously collecting a released-drug sample solution received from release environment assembly 22.

Figure 2B:
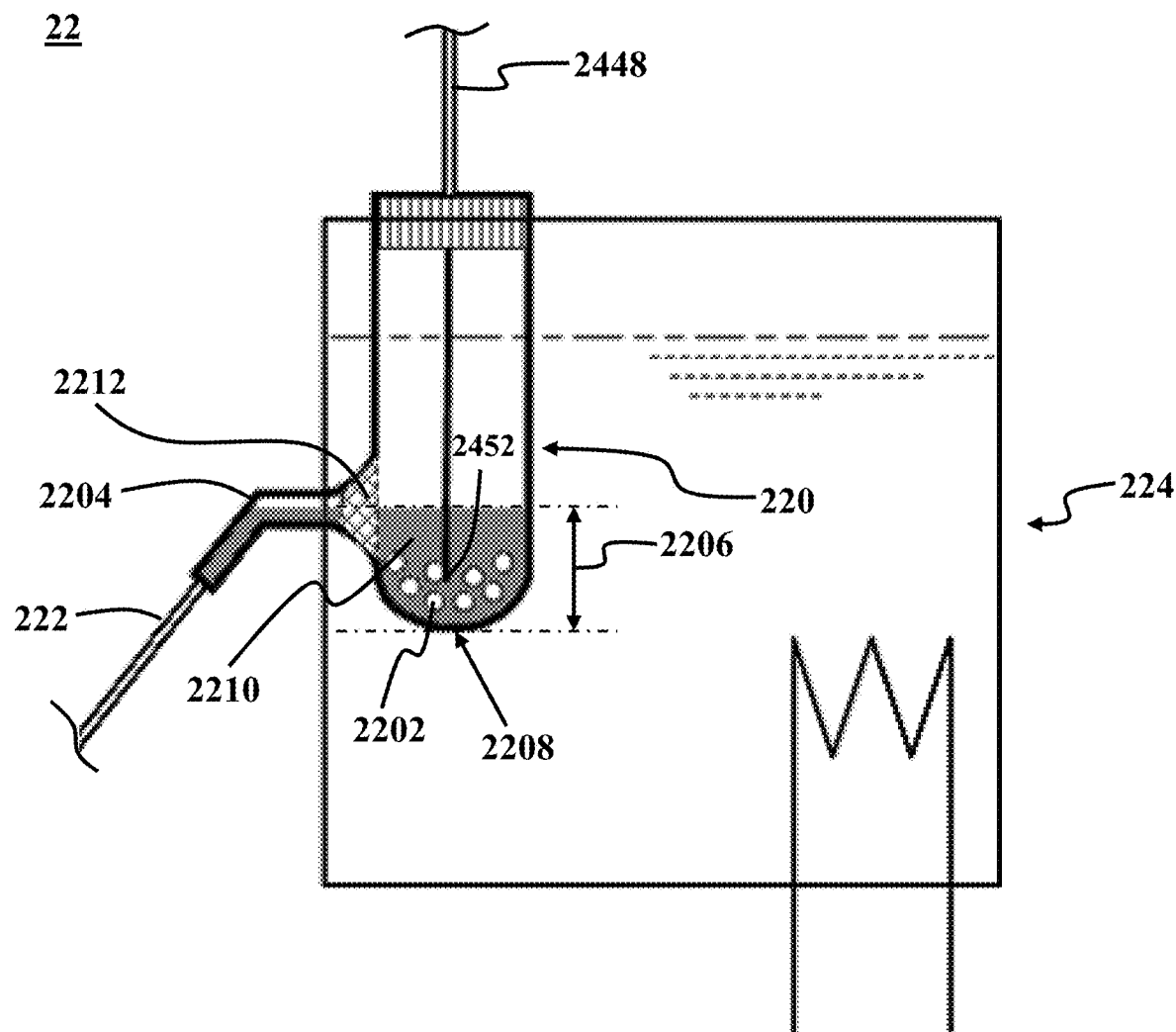
FIG. 2B illustrates a sectional view of release environment assembly, consistent with an exemplary embodiment of the present disclosure.

FIG. 2B illustrates a sectional view of release environment assembly 22, consistent with an exemplary embodiment of the present disclosure. Release environment assembly 22 may include an overflow cell 220 that may be similar to flow cell 120 of FIG. 1. Referring to FIG. 2B, in an exemplary embodiment, overflow cell 220 may provide a release environment in which the dissolution medium may be put in contact with a dosage form 2202 to allow dosage form 2202 to be gradually released into the dissolution medium and form a sample solution. Overflow cell 220 may include an overflow outlet port 2204 that may be at a predetermined height 2206 from a bottom 2208 of overflow cell 220. A dosage form 2202 may be disposed within overflow cell 220 adjacent bottom 2208 of overflow cell 220 below overflow outlet port 2204.

Figure 2C:
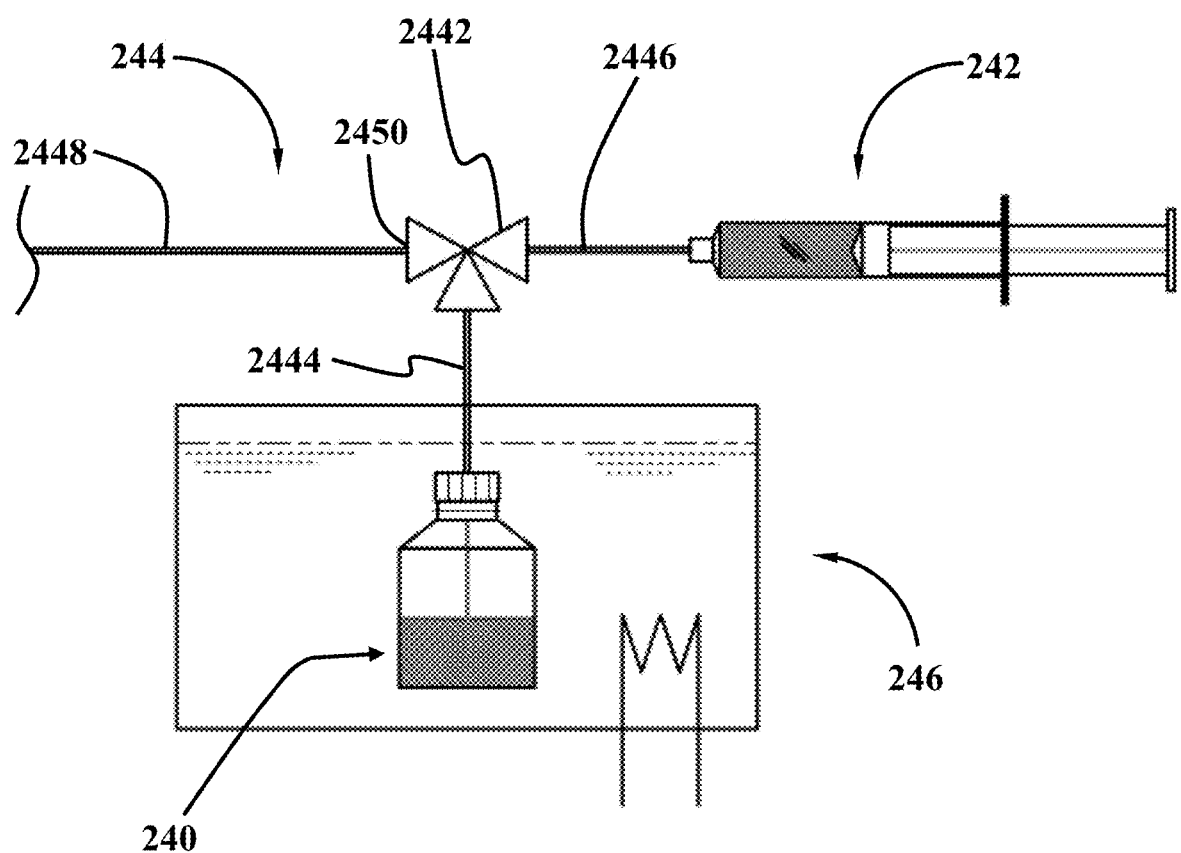
FIG. 2C illustrates a sectional view of dissolution medium supply assembly, consistent with an exemplary embodiment of the present disclosure.

FIG. 2C illustrates a sectional view of dissolution medium supply assembly 24, consistent with an exemplary embodiment of the present disclosure. Dissolution medium supply assembly 24 may include a dissolution medium reservoir 240 that may be similar to dissolution medium reservoir 140 of FIG. 1. In an exemplary embodiment, dissolution medium reservoir 240 may contain a fresh dissolution medium, such as a phosphate buffer with a pH similar to the pH of bodily fluids.

In an exemplary embodiment, dissolution medium supply assembly 24 may further include a dissolution medium pump 242 that may be connected in fluid communication with dissolution medium reservoir 240. In an exemplary embodiment, dissolution medium supply assembly 24 may further include a dissolution medium path 244 that may be controlled by a three-way valve 2442. Dissolution medium path 244 may include a supply line 2444, a pump line 2446, and an injection line 2448. In an exemplary embodiment, dissolution medium reservoir 240 may be connected in fluid communication with dissolution medium pump 242 via supply line 2444 and pump line 2446. Dissolution medium pump 242 may pump the dissolution medium out of dissolution medium reservoir 240 via supply line 2444 and pump line 2446. In an exemplary embodiment, dissolution medium pump 242 may pressurize the dissolution medium and pump the pressurized dissolution medium through injection line 2448.

Referring to FIGS. 2B and 2C, in an exemplary embodiment, injection line 2448 may include an input end 2450 connected in fluid communication with pump line 2446 via three-way valve 2442 and an output end 2452 connected in fluid communication with overflow cell 220. In an exemplary embodiment, dissolution medium pump 242 may be a reciprocating pump such as a syringe pump that may pump in the dissolution medium via supply line 2444 and pump line 2446 while injection line 2448 is disconnected from pump line 2446 by three-way valve 2442. After that, dissolution medium pump 242 may pump the dissolution medium into overflow cell 220 via pump line 2446 and injection line 2448, while supply line 2444 is disconnected from pump line 2446 by three-way valve 2442.

Referring to FIG. 2B, in an exemplary embodiment, output end 2452 of injection line 2448 may be inserted into overflow cell 220 such that output end 2448 is adjacent bottom 2208 of overflow cell 220 below overflow outlet port 2204. Pressurized dissolution medium may be injected into overflow cell 220 via injection line 2448. Overflow cell 220 may provide a release environment 2210 with a predetermined volume. In an exemplary embodiment, the volume of the release environment 2210 may be determined by adjusting predetermined height 2206. Dosage form 2202 may gradually dissolve in the dissolution medium and form a sample solution. As fresh dissolution medium is being pumped into overflow cell 220, the sample solution is urged out of overflow cell 220 via a discharge line 222 that may be connected in fluid communication with overflow outlet port 2204.

In an exemplary embodiment, overflow cell 220 may further include a filter 2212 that may be positioned within overflow outlet port 2204. Filter 2212 may retain undissolved dosage form within overflow cell 220. In an exemplary embodiment, filter 2212 may be a glass fiber or glass wool filter, which may retain undissolved dosage forms, especially insoluble or sticky drug particles within overflow cell 220 without creating a significant backpressure.

In an exemplary embodiment, overflow cell 220 may be submerged in a first water bath 246. First water bath 246 may be similar to first temperature controller 122 of FIG. 1 that may be configured to control and maintain a temperature of release environment 2210 at a first predetermined temperature. In an exemplary embodiment, the temperature of first water bath 246 may be adjustable between 20° C. and 50° C. In an exemplary embodiment, first water bath 246 may be configured to control and maintain the temperature of release environment 2210 at 37±1° C., a temperature value similar to a human body condition.

Referring to FIG. 2C, in an exemplary embodiment, dissolution medium reservoir 240 may be submerged in a second water bath 246. Second water bath 246 may be similar to second temperature controller 144 of FIG. 1 that may be configured to control and maintain a temperature of dissolution medium reservoir 240 at a second predetermined temperature. In an exemplary embodiment, the second predetermined temperature may be similar to the first predetermined temperature in order to avoid a temperature shock when the dissolution medium is injected to overflow cell 220 to contact the dosage form in the release environment. In an exemplary embodiment, the temperature of second water bath 246 may be adjustable between 20° C. and 50° C. As mentioned before, a temperature shock may be harmful to sensitive drug molecules in the release environment, therefore, in an exemplary embodiment, the temperature of dissolution medium reservoir 240 may be controlled and maintained at 37±1° C. by second water bath 246.

Figure 2D:
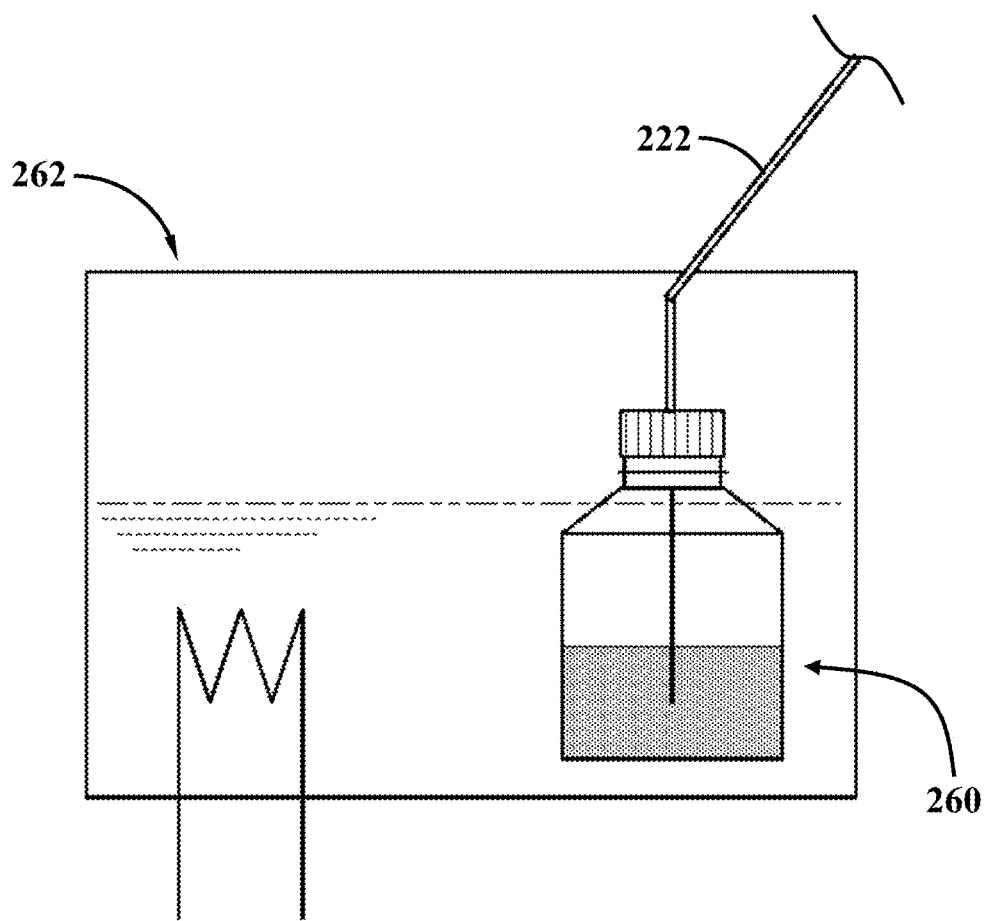
FIG. 2D illustrates a sectional view of sample collection assembly, consistent with an exemplary embodiment of the present disclosure.

FIG. 2D illustrates a sectional view of sample collection assembly 26, consistent with an exemplary embodiment of the present disclosure. Sample collection assembly 26 may include a sample collection vessel 260 similar to sample collection vessel 160 of FIG. 1. Referring to FIGS. 2B and 2D, in an exemplary embodiment, sample collection vessel 260 may be connected in fluid communication with overflow outlet port 2204 of overflow cell 220 via discharge line 222 and may collect the sample solution received from overflow cell 220 via discharge line 222. Sample collection assembly 26 may further include a third water bath 262 that may be similar to third temperature controller 162 of FIG. 1.

In an exemplary embodiment, third water bath 262 may be utilized for controlling and maintaining a temperature of sample collection vessel 260 at a third predetermined temperature. In an exemplary embodiment, third water bath 262 may be configured for controlling and maintaining a temperature in a range of −20° C. to 20° C. In an exemplary embodiment, the third predetermined temperature may be a temperature at which the targeted chemical contained in the dosage form is the most stable, for example, the third predetermined temperature may be in a range of 2° C. to 8° C.

Figure 3:
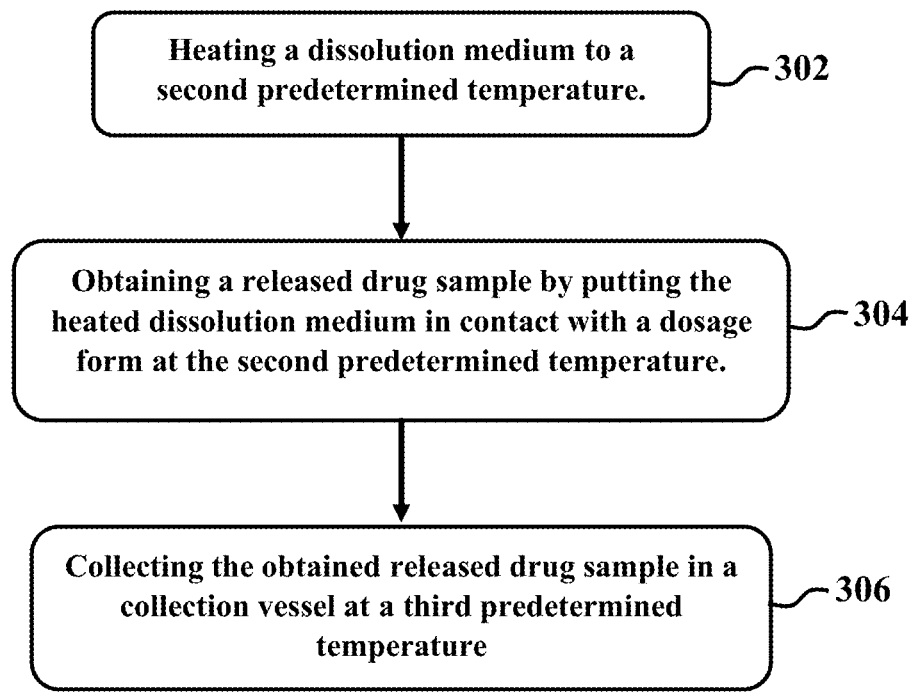
FIG. 3 illustrates a method for performing a dissolution test, consistent with one or more exemplary embodiment of the present disclosure.

FIG. 3 illustrates a method 300 for performing a dissolution test, consistent with one or more exemplary embodiment of the present disclosure. Method 300 may include a step 302 of heating a dissolution medium to a second temperature, a step 304 of obtaining a released drug sample by putting the heated dissolution medium in contact with a dosage form at the second temperature, and a step 306 of collecting the obtained released drug sample in a collection vessel at a third temperature.

FIG. 3 in combination with FIGS. 2A-2D illustrate the functionality in light of structure of dissolution test apparatus 20, consistent with one or more exemplary embodiments of the present disclosure. In an exemplary embodiment, dissolution test apparatus 20 may be utilized for implementing method 300. Step 302 may include heating a dissolution medium to a second temperature. For example, the dissolution medium may be poured into dissolution medium reservoir 240 which may be submerged in second water bath 246 and then second water bath 246 may be configured to maintain the temperature of dissolution medium reservoir 240 at the second temperature. In dissolution tests performed for the drugs, since the purpose of performing the test is to evaluate the drug release in human body, the test is performed at a temperature of approximately 37° C. to simulate the temperature of human body. In an exemplary embodiment, the second temperature may be 37±1° C.

According to one or more exemplary embodiments, the dissolution medium may be an acetate buffer, HCl, a phosphate buffer, a potassium phosphate monobasic buffer, sodium chloride, sodium dihydrogenphsphate monohydrate, simulated gastric fluid, simulated intestinal fluid, hydroxypropyl-beta-cyclodextrin, water, and mixtures thereof. Table 1 illustrates a few exemplary dissolution media for different drugs with different dosage forms.

TABLE 1

Dissolution media examples

| Drug | Dosage Form | Dissolution Media |
|---|---|---|
| Acetazolamide | Capsule (Extended Release) | Acetate Buffer, pH 4.5 with 2.2% Tween 20 |
| Albuterol Sulfate | Tablet (Extended Release) | 0.1N HCl |
| Alfuzosin HCl | Tablet (Extended Release) | 0.01N HCl |
| Alprazolam | Tablet (Extended Release) | 1% Phosphate Buffer, pH 6.0 |
| Amoxicillin | Tablet (Extended Release) | 3 Stage dissolution: 50 mM potassium phosphate monobasic buffer at pH 4.0 (0-2 hours), 6.0 (2-4 hours) and 6.8 (4 hours and beyond) |
| Amphetamine Aspartate/Amphetamine Sulfate/Dextroamphetamine Saccharate/Dextroamphetamine Sulfate | Capsule (Extended Release) | Dilute HCl, pH 1.1 for first 2 hrs, then add 200 mL of 200 mM Phosphate Buffer and adjust to pH 6.0 for the remainder |
| Amphetamine Aspartate/Amphetamine Sulfate/Dextroamphetamine Saccharate/Dextroamphetamine Sulfate [12.5, 25, 37.5, 50 mg] | Capsule (Extended Release) | Media 1: pH 1.1 ± 0.1, Dilute HCl 2 hours; Media 2: pH 6.0 ± 0.1, Phosphate Buffer 3rd hour, Media 3: pH 7.5 ± 0.1, Phosphate Buffer for the remainder |
| Aspirin | Capsule (Extended Release) | 0.05M Potassium Phosphate Buffer (pH 7.4) with trypsin (.001% w/v) and sodium azide (.025% w/v) |
| Budesonide | Tablet (Extended Release) | Acid Stage: 0.1M HCl containing 0.5% Macrogol Cetostearyl Ether; Buffer Stage: pH 7.2 phosphate buffer containing 0.5% Macrogol Cetostearyl Ether. |
| Buprenorphine | Film, Transdermal (Extended Release) | 0.9% Sodium Chloride at 32° C. |
| Buprenorphine HCl | Implant | Water |
| Calcifediol | Capsule (Extended Release) | 0.5% SDS in 5 mM Sodium Dihydrogenphosphate Monohydrate, pH 6.8 |
| Carbamazepine | Capsule (Extended Release) | First 4 hours: Dilute Acid, pH 1.1. After 4 hours: Phosphate Buffer, pH 7.5 with 0.1% sodium lauryl sulfate (SLS). |
| Carbidopa/Levodopa | Tablet (Extended Release) | 0.1N HCl |
| Carvedilol Phosphate | Capsule (Extended Release) | 0.1N HCl |
| Chlorpheniramine Maleate/Codeine Phosphate | Tablet (Extended Release) | Simulated gastric fluid (SGF) without enzyme (pH 1.2) |
| Chlorpheniramine Polistirex/Hydrocodone Polistirex | Capsule (Extended Release) | Simulated Intestinal Fluid without enzyme |
| Clonidine (0.1 mg) | Tablet (Extended Release) | Acid stage: 0.01N HCl; Buffer stage: Phosphate Buffer, pH 7.0 |
| Clonidine (EQ. 0.17 mg and EQ. 0.26 mg) | Tablet (Extended Release) | 500 mL 0.1N HCl for the 1st hour, then add 400 mL 0.27M Sodium Phosphate (Dibasic) buffer solution |
| Dasabuvir Na/Ombitasvir/Paritaprevir/Ritonavir | Tablet (Extended Release) | 15 mM hexadecyltrimethylammonium bromide (CTAB) in 0.03M Sodium Phosphate Buffer, pH 6.8 |
| Estradiol (Test 1) (0.025 mg/24 hr, 0.0375 mg/24 hr, 0.05 mg/24 hr, 0.075 mg/24 hr and 0.1 mg/24 hr) | Film, Transdermal (Extended Release) | Water at 32 ± 0.5° C. |

TABLE 1-continued

Dissolution media examples

| Drug | Dosage Form | Dissolution Media |
| --- | --- | --- |
| Ethinyl Estradiol; Norelgestromin | Film, Transdermal | 0.1% Hydroxypropyl-beta-cyclodextrin at 32° C. |
| Granisetron | Film, Transdermal (Extended Release) | 80 microL/L phosphoric acid (85%) at 32 ± 0.5° C. |
| Rivastigmine | Film, Transdermal | 0.9% NaCl at 32° C. |
| Testosterone | Film, Transdermal (Extended Release) | 0.1M sodium chloride containing 2.5% (v/v) of Tween 40 at 32 ± 0.5° C. |
| Testosterone | Buccal Tablet (Extended Release) | 1% sodium dodecyl sulfate in double distilled water |

In an exemplary embodiment, step 304 may include obtaining a released drug sample by putting the heated dissolution medium in contact with a dosage form at the second temperature. For example, dosage form 2202 may be placed within overflow cell 220 and overflow cell 220 may be submerged within first water bath 224. First water bath 224 may be configured to maintain the temperature of overflow cell 220 at the second temperature. Dissolution medium pump 242 may then be utilized for pumping the heated dissolution medium from dissolution medium reservoir 240 into overflow cell 220 via dissolution medium path 244. This way, the heated dissolution medium may be put in contact with dosage form 2202 within overflow cell 220. In an exemplary embodiment, the dissolution medium may be pumped into overflow cell 220 by dissolution medium pump 242 with a predetermined flow rate.

In an exemplary embodiment, the predetermined flowrate may be proportional to the volume of the dissolution medium in overflow cell 220 which is determined by the predetermined height of overflow outlet port 2204. In an exemplary embodiment, the predetermined flow rate may be calculated by Equation (1) below:

$$Q_{dissolution\ medium} = \frac{V_{dissolution\ medium}}{t_{stability\ of\ drug}} \quad \text{Equation (1)}$$

$Q_{dissolution\ medium}$ is the predetermined flow rate at which dissolution medium pump 242 may pump the dissolution medium into overflow cell 220 via dissolution medium path 244, $V_{dissolution\ medium}$ is the volume of dissolution medium in overflow cell 220 which may partially depend on the predetermined height of overflow outlet port 2204 from bottom 2208 of overflow cell 220 and of course the diameter of overflow cell 220, and $t_{stability\ of\ drug}$ is the stability of the drug in the dissolution medium under test conditions. For example, dantrolene sodium is stable for 1 hour in a phosphate buffer with a pH of 7.4 and at a temperature of approximately 37° C., utilizing Equation (1) above, in an overflow cell in which the volume of the phosphate buffer is approximately 2 mL $Q_{dissolution\ medium}$ may be 2 mL/h. Table 2 illustrates different injection flow rates for different drugs in an exemplary overflow cell with a volume of approximately 2 mL.

TABLE 2

Exemplary dissolution medium flow rates calculated by Equation (2).

| Drug | Dissolution Medium | $t_{stability\ of\ drug}$ | $Q_{dissolution\ medium}$ |
| --- | --- | --- | --- |
| Dantrolene | Buffer with pH 7.4 | 1 hour at 37° C. | 2 mL/h |
| Omeprazole | phosphate buffer pH 7.5 | <10 hours at 37° C. | 0.2 mL/h |
| IGF-I | serum | <10 hours at 37° C. | 0.2 mL/h |
| Taxol | Water with PH 4/7 | 6 hours at 37° C. | 0.3 mL/h |
| Insulin | PBS buffer pH = 7.4 | 2 hours at 37° C. | 1 mL/h |
| hGH | PBS buffer pH = 7.4 | 1 hour at 37° C. | 2 mL/h |

In an exemplary embodiment, step 306 may include collecting the obtained released drug sample in a collection vessel at a second temperature. For example, the obtained released drug sample may overflow out of overflow cell 220 through overflow outlet port 2204. Discharge line 222 which may be connected to overflow outlet port 2204 may deliver the obtained released drug sample into sample collection vessel 260 which is submerged in third water bath 262. Third water bath 262 may be configured to maintain the temperature of sample collection vessel 260 at a second temperature. In dissolution tests performed for temperature-sensitive drugs, the drugs are only stable in the dissolution medium at 37° C. for a limited period of time. Therefore, in long-term release evaluations of the drugs, a large number of tests must be performed due to their limited stability at high temperatures. In an exemplary embodiment, the temperature of the obtained released drug sample within sample collection vessel 260 may be maintained at a temperature at which the released drug sample is the most stable. For example, the third temperature may be in a range of 2° C. to 8° C.

EXAMPLE

In this example, exemplary systems and methods were used for performing dissolution tests on human growth hormone (hGH), consistent with an exemplary embodiment of the present disclosure. The release performance of hGH was evaluated for a 14-day period. First, the stability of hGH in a phosphate buffer at 37±1° C. was tested. To this end, a 0.01 ppm hGH solution in a 0.05 M phosphate buffer with a pH=7.4 was prepared. The prepared hGH solution was maintained at a temperature of approximately 37±1° C. and stability analyses were performed at 0, 1, 2, 3, 4, 6, 12, and 24 hours.

Figure 4:
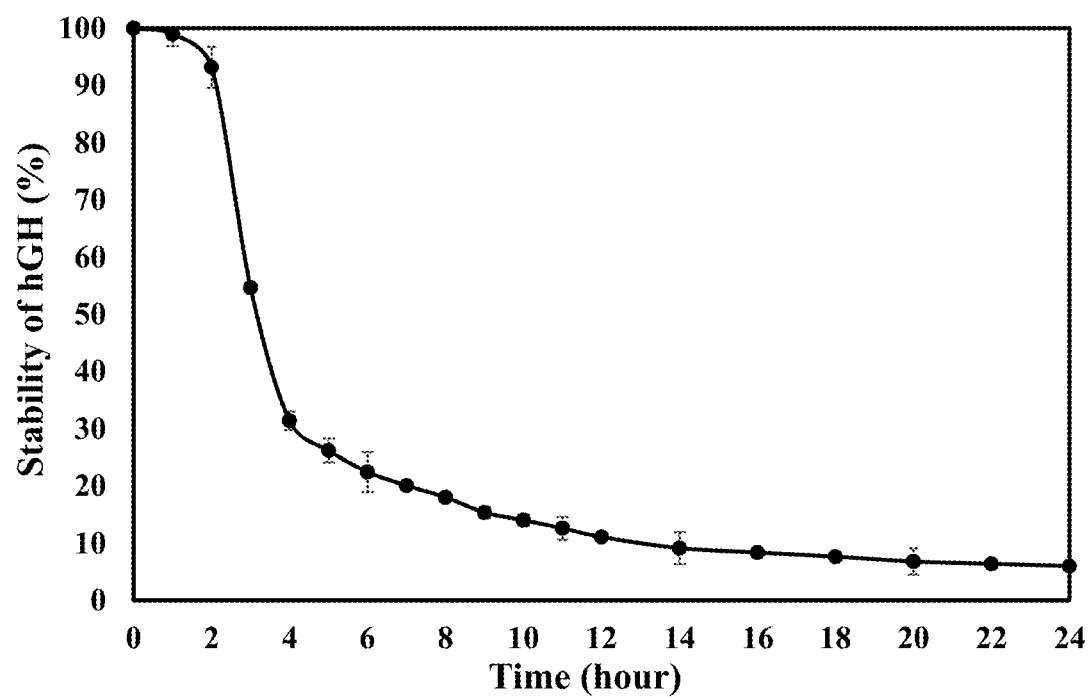
FIG. 4 illustrates an hGH stability versus time graph obtained from stability tests performed at 37±1° C., consistent with one or more exemplary embodiments of the present disclosure.

FIG. 4 illustrates an hGH stability versus time graph obtained from stability tests performed at 37±1° C., consistent with one or more exemplary embodiments of the present disclosure. As can be seen, hGH stability decreases after 2 hours, which means that the prepared hGH solution in phosphate buffer is stable at 37±1° C. only for 2 hours. Therefore, if a dissolution test was to be performed by available USP apparatuses, the hGH solution would have to be prepared, sampled and analyzed every 2 hours, which means for a dissolution evaluation that needs to be performed during a 14-day period, at least 168 dissolution tests must be performed.

The stability of hGH was then tested in a phosphate buffer at 5±2° C. To this end, a 0.01 ppm hGH solution in a 0.05 M phosphate buffer with a pH=7.4 was prepared. The prepared hGH solution was maintained at a temperature of approximately 5±2° C. and stability analyses were performed at 0, 1, 2, 3, 4, and 5 days.

Figure 5:
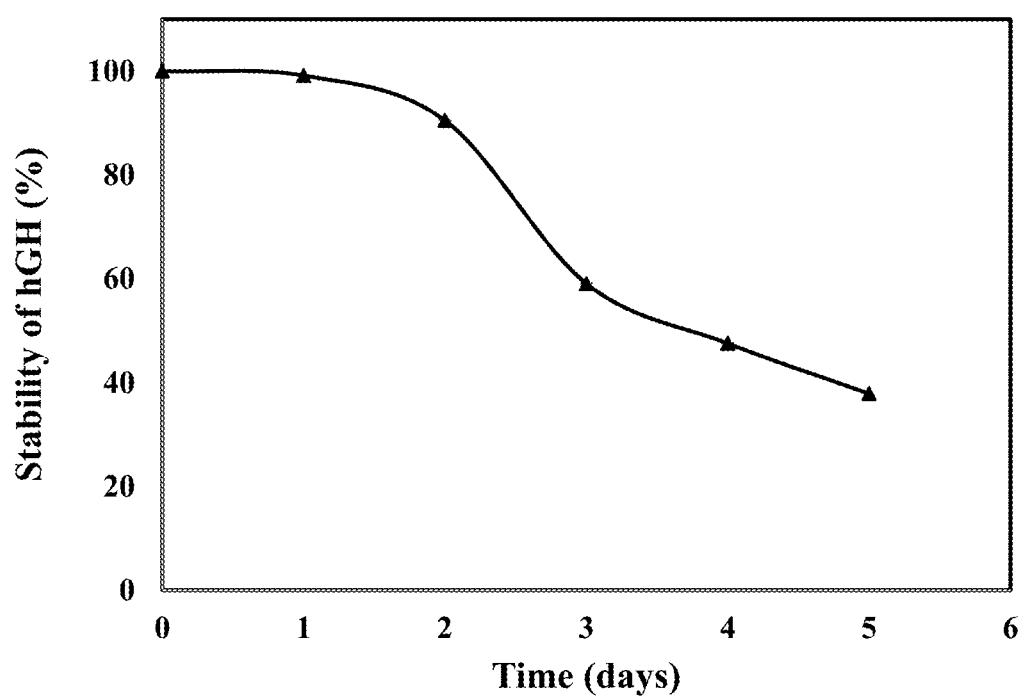
FIG. 5 illustrates an hGH stability versus time graph obtained from stability tests performed at 5±2° C., consistent with one or more exemplary embodiments of the present disclosure.

FIG. 5 illustrates an hGH stability versus time graph obtained from stability tests performed at 5±2° C., consistent with one or more exemplary embodiments of the present disclosure. As can be seen, hGH stability decreases after 1 day, which means that the prepared hGH solution in phosphate buffer is stable at 5±2° C. for 1 day. The increased stability of the hGH solution at a lower temperature of 5±2° C. allows for sampling and analysis of hGH solution every 24 hour, which means for a period of 14 days only 14 sampling and analysis would be required.

In this example, an exemplary dissolution test apparatus similar to dissolution test apparatus 20 of FIGS. 2A-2D was utilized for evaluating the dissolution performance of hGH for a 14-day period. For purpose of clarity the dissolution test procedure is described with reference to FIGS. 2A-2D. A 0.05 M phosphate buffer with a pH of 7.4 was poured into dissolution medium reservoir 240. Second water bath 246 was configured to maintain a temperature of approximately 37° C. In this example, dissolution medium reservoir 240 along with dissolution medium path 244 were submerged in second water bath 246 in order to increase the temperature of the phosphate buffer to approximately 37° C. A dosage form containing hGH was placed in overflow cell 220 as dosage form 2202 and first water bath 224 was configured to maintain a temperature of approximately 37° C. After that, dissolution medium pump 242 was utilized to pump the phosphate buffer into overflow cell 220 with a flow rate of approximately 2 mL/h. Sample solution was collected in sample collection vessel 260 and third water bath was configured to maintain a temperature of approximately 5° C. Due to stability of the sample solution collected and maintained at 5° C., analysis was performed on the collected sample solution every 24 hours during the 14-day period instead of every 2 hours which is the case in official USP apparatus.

Therefore, exemplary apparatus consistent with one or more exemplary embodiments of the present disclosure allows for monitoring the release of a temperature-sensitive drug during a relatively long period of 14 days by performing only 14 analyses, which is a significant amount of time and effort saved in comparison with the test procedure performed in a standard dissolution test apparatus such as USP apparatus 4, in which at least 168 analyses must be performed to monitor the release of a temperature-sensitive drug during 14 days. This is due to the ability of maintaining the sample solution in a stable state by keeping sample collection vessel 260 at 5° C. which is a temperature at which hGH is the most stable.

While the foregoing has described what are considered to be the best mode and/or other examples, it is understood that various modifications may be made therein and that the subject matter disclosed herein may be implemented in various forms and examples, and that the teachings may be applied in numerous applications, only some of which have been described herein. It is intended by the following claims to claim any and all applications, modifications and variations that fall within the true scope of the present teachings.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 103 of the patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

It will be understood that the terms and expressions used herein have the ordinary meaning as is accorded to such terms and expressions with respect to their corresponding respective areas of inquiry and study except where specific meanings have otherwise been set forth herein. Relational terms such as first and second and the like may be used solely to distinguish one entity or action from another without necessarily requiring or implying any actual such relationship or order between such entities or actions. The terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus. An element proceeded by "a" or "an" does not, without further constraints, preclude the existence of additional identical elements in the process, method, article, or apparatus that comprises the element.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various implementations. This is for purposes of streamlining the disclosure, and is not to be interpreted as reflecting an intention that the claimed implementations require more features than are expressly recited in each claim. Rather, as the following claims reflect, inventive subject matter lies in less than all features of a single disclosed implementation. Thus, the following claims are hereby incorporated into the Detailed Description, with each claim standing on its own as a separately claimed subject matter.

While various implementations have been described, the description is intended to be exemplary, rather than limiting and it will be apparent to those of ordinary skill in the art that many more implementations and implementations are possible that are within the scope of the implementations. Although many possible combinations of features are shown in the accompanying figures and discussed in this detailed description, many other combinations of the disclosed features are possible. Any feature of any implementation may be used in combination with or substituted for any other feature or element in any other implementation unless specifically restricted. Therefore, it will be understood that any of the features shown and/or discussed in the present disclosure may be implemented together in any suitable combination. Accordingly, the implementations are not to be restricted except in light of the attached claims and their equivalents. Also, various modifications and changes may be made within the scope of the attached claims.

What is claimed is:

1. A dissolution test apparatus, comprising:
   an overflow vessel with an overflow outlet port at a predetermined height from a bottom of the vertical overflow vessel;
   a first water bath submerging the flow cell, the first water bath configured to keep a temperature of the flow cell at a first predetermined temperature;
   a pressurized vessel containing a dissolution medium;
   a second water bath submerging the pressurized vessel, the second water bath configured to keep the dissolution medium at a second predetermined temperature;
   a dissolution medium path including an output end connected in fluid communication with the flow cell and an input end attached in fluid communication to the pressurized vessel, the dissolution medium path configured to transfer the dissolution medium from the pressurized vessel into the flow cell;
   a collection vessel connected to the overflow outlet port of the flow cell; and
   a third water bath submerging the collection vessel, the third water bath configured to keep the collection vessel at a third predetermined temperature.

2. The apparatus of claim 1, wherein the output end of the dissolution medium path is positioned within the overflow vessel adjacent the bottom of the overflow vessel and wherein the overflow vessel configured to receive the injected dissolution via the dissolution medium path.

3. The apparatus of claim 1, wherein the pressurized vessel comprises:
   a dissolution medium reservoir containing a dissolution medium; and
   a dissolution medium pump in fluid communication with the dissolution reservoir, the dissolution medium pump configured to pressurize the dissolution medium.

4. The apparatus of claim 1, wherein the overflow vessel further containing a dosage form placed at the bottom of the overflow vessel below the overflow outlet port, the dosage form configured to form a released drug sample by being put in contact with the dissolution medium.

5. The apparatus of claim 4, wherein the released drug sample is continuously discharged via the overflow outlet port responsive to a height of released drug sample reaching the predetermined height.

6. The apparatus of claim 5, wherein the overflow vessel further comprises a filter positioned at the overflow outlet port, the filter configured to retain undissolved dosage form within the vertical overflow vessel.

7. The apparatus of claim 1, wherein the first predetermined temperature is equal to the second predetermined temperature.

8. The apparatus of claim 1, wherein the second predetermined temperature is between 20° C. and 50° C.

9. The apparatus of claim 1, wherein the second predetermined temperature is 37±1° C.

10. The apparatus of claim 1, wherein the third predetermined temperature is between 2 and 8° C.

11. The apparatus of claim 1, wherein the dissolution medium comprises a phosphate buffer.

12. A dissolution test method, comprising:
    heating a dissolution medium to a second predetermined temperature;
    obtaining a released drug sample by putting the heated dissolution medium in contact with a dosage form, wherein putting the heated dissolution medium in contact with the dosage form comprises continuously injecting the heated dissolution medium into an overflow vessel with an overflow outlet port at a predetermined height from a bottom of the vertical overflow vessel and wherein the dosage form is placed at the bottom of the vertical overflow vessel below the overflow outlet port; and
    collecting the obtained released drug sample in a collection vessel at a third predetermined temperature,
    wherein, the overflow vessel is kept at the second predetermined temperature by submerging the overflow vessel in a water bath at the second predetermined temperature.

13. The method according to claim 12, further comprising retaining undissolved dosage form within the vertical overflow vessel by filtering the obtained released drug sample.

14. The method of claim 12, wherein the second predetermined temperature is between 20° C. and 50° C.

15. The method of claim 11, wherein the second predetermined temperature is 37±1° C.

16. The method of claim 12, wherein the dissolution medium comprises a phosphate buffer.

17. The method of claim 12, wherein the third predetermined temperature is between −20 and 20° C.

18. The method of claim 12, wherein the third predetermined temperature is between 2 and 8° C.

* * * * *